(12) United States Patent  
Gildenhuys et al.

(10) Patent No.: US 9,017,522 B2  
(45) Date of Patent: Apr. 28, 2015

(54) SEPARATION OF COMPONENTS FROM A MULTI-COMPONENT HYDROCARBON STREAM WHICH INCLUDES ETHYLENE

(75) Inventors: Johannes Jochemus Gildenhuys, Johannesburg (ZA); Andrew Kenneth Stone, Johannesburg (ZA); William Francis Revelt, Missouri City, TX (US)

(73) Assignee: Sasol Technolgy (Proprietary) Limited, Johannesburg (ZA)

( * ) Notice: Subject to any disclaimer, the term of this patent is extended or adjusted under 35 U.S.C. 154(b) by 556 days.

(21) Appl. No.: 13/501,116

(22) PCT Filed: Oct. 1, 2010

(86) PCT No.: PCT/IB2010/054444  
§ 371 (c)(1),  
(2), (4) Date: Apr. 10, 2012

(87) PCT Pub. No.: WO2011/045701  
PCT Pub. Date: Apr. 21, 2011

(65) Prior Publication Data  
US 2012/0199467 A1 Aug. 9, 2012

(30) Foreign Application Priority Data  
Oct. 16, 2009 (ZA) ................................ 2009/07265

(51) Int. Cl.  
*C07C 2/08* (2006.01)  
*C07C 7/04* (2006.01)  
*B01D 3/06* (2006.01)  
(Continued)

(52) U.S. Cl.  
CPC ... *C07C 2/08* (2013.01); *B01D 3/32* (2013.01); *B01D 3/06* (2013.01); *C07C 11/04* (2013.01); *C07C 7/04* (2013.01)

(58) Field of Classification Search  
CPC ............ C07C 2/08; C07C 7/04; C07C 11/04; B01D 3/06; B01D 3/32  
USPC .......... 203/2, 71, 77, 80, 88, 91; 208/62, 133; 585/502  
See application file for complete search history.

(56) References Cited

U.S. PATENT DOCUMENTS 3,391,219 A 7/1968 Davis et al.  
3,663,647 A * 5/1972 Lanier ........................... 585/316  
(Continued)

FOREIGN PATENT DOCUMENTS

GB 1 019 411 A 2/1966

*Primary Examiner* — Nina Bhat  
*Assistant Examiner* — Jonathan Miller  
(74) *Attorney, Agent, or Firm* — Sutherland Asbill & Brennan LLP (57) ABSTRACT

A process to separate a multi-component hydrocarbon stream which includes ethylene and other components with at least some of the components being present in a number of phases, is provided. The process includes in a first flash stage, flashing the multi-component hydrocarbon stream, from an elevated pressure and temperature to a pressure in the range of 10-18 bar(a), producing a first ethylene-containing vapor stream at a pressure in the range of 10-18 bar(a) and a multi-phase stream which includes some ethylene. In a second flash stage, the multi-phase stream is flashed to a pressure of less than 6 bar(a), producing a second vapor stream at a pressure of less than 6 bar(a) and a bottoms stream. The first ethylene-containing vapor stream is removed from the first flash stage, the second vapor stream is removed from the second flash stage and the bottoms stream is removed from the second flash stage.

12 Claims, 2 Drawing Sheets (51) Int. Cl.
   *B01D 3/32* (2006.01)
   *C07C 11/04* (2006.01)

(56) References Cited

U.S. PATENT DOCUMENTS

| | | |
|---|---|---|
| 3,789,081 A | 1/1974 | Lanier |
| 3,906,053 A * | 9/1975 | Lanier .......................... 585/316 |
| 4,589,957 A * | 5/1986 | Sherk et al. ..................... 203/75 |
| 4,929,788 A * | 5/1990 | Huang et al. ................... 585/522 |
| 7,582,723 B2 * | 9/2009 | Penzo et al. .................. 528/483 |
| 8,636,831 B2 * | 1/2014 | Van Der Schrick et al. .... 95/186 |
| 2010/0268006 A1 * | 10/2010 | Gildenhuys ................... 585/313 |

\* cited by examiner

SEPARATION OF COMPONENTS FROM A MULTI-COMPONENT HYDROCARBON STREAM WHICH INCLUDES ETHYLENE

TECHNICAL FIELD

THIS INVENTION relates to separation of components from a multi-component hydrocarbon stream which includes ethylene. In particular, the invention relates to a process to separate a multi-component hydrocarbon stream which includes components in a plurality of phases and ethylene, and to an ethylene oligomerisation process which includes this separation process.

BACKGROUND OF THE INVENTION

Distillation is the method of choice for many processes to separate a multi-component hydrocarbon stream into different fractions. When the multi-component hydrocarbon stream includes solids, whether molten, dissolved or not dissolved, such as polymers and waxes, it is undesirable to feed the multi-component hydrocarbon stream over distillation trays, as the solids may block the trays. One example of such a multi-component hydrocarbon stream is the oligomeric product stream obtained from the oligomerisation of an olefinic feedstock. An efficient and economical process to separate a multi-component hydrocarbon stream, which may include solids, would thus be desirable.

SUMMARY OF THE INVENTION

According to one aspect of the invention, there is provided a process to separate a multi-component hydrocarbon stream which includes ethylene and other components with at least some of the components being present in a plurality of phases, the process including in a first flash stage, flashing the multi-component hydrocarbon stream, from an elevated pressure (i.e. a pressure of more than 18 bar(a)) and an elevated temperature (i.e. a temperature of more than 180° C.) to a pressure in the range of 10-18 bar(a), producing a first ethylene-containing vapour stream at a pressure in the range of 10-18 bar(a) and a multiphase stream which includes some ethylene;

in a second flash stage, flashing the multi-phase stream to a pressure of less than 6 bar(a), producing a second vapour stream at a pressure of less than 6 bar(a) and a bottoms stream;

removing the first ethylene-containing vapour stream from the first flash stage and the second vapour stream from the second flash stage; and removing the bottoms stream from the second flash stage.

In at least one embodiment of the invention, the process includes reheating the multi-phase stream from the first flash stage before flashing the multi-phase stream in the second flash stage.

According to a second aspect of the invention, there is provided an ethylene oligomerisation process, the process including in an oligomerisation stage, oligomerising ethylene and withdrawing a multi-component hydrocarbon stream of different phases which includes oligomeric product, polymeric product, and unreacted ethylene;

heating the multi-component hydrocarbon stream to a temperature in excess of 180° C.;

separating the multi-component hydrocarbon stream in accordance with a separation process as hereinbefore described producing said first ethylene-containing vapour stream; and feeding the first ethylene-containing vapour stream to an ethylene recovery stage producing an ethylene-rich stream and an ethylene-poor multi-component hydrocarbon stream which includes oligomeric and/or polymeric product.

The process may include the step of recovering energy from the first ethylene-containing vapour stream by heat exchange with a second stream, which second stream may be or may include the multi-component hydrocarbon stream, a further process stream or a utility stream. Typically, the first ethylene-containing vapour stream is at least partially condensed during such a heat exchange step.

The multi-phase stream may be predominantly a liquid stream which includes solids, and optionally entrained gas.

In this specification, the term "solids" is intended to include materials such as polyethylene, waxes, catalysts and catalyst de-activation products, whether molten, partially molten or dissolved at the process conditions of the multi-component hydrocarbon stream. Furthermore, in this specification the term "condense" includes a phase change from gas to liquid and the term "compress" does not include a phase change.

The multi-phase stream is preferably flashed in the second flash stage to a pressure of between about 1 bar(a) and about 6 bar(a), more preferably between about 2 bar(a) and about 5 bar(a), e.g. between about 2 bar(a) and about 4 bar(a). In some embodiments of the invention however, a negative gauge pressure, i.e. a subatmospheric pressure, may be used in the second flash stage.

Preferably, in the first flash stage, the multi-component hydrocarbon stream is flashed from an elevated temperature of at least 185° C., preferably an elevated temperature of at least 190° C., more preferably an elevated temperature of at least 195° C., and an elevated pressure of more than 30 bar(a). The first ethylene-containing vapour stream is thus typically defining a higher mass flow of ethylene and is at a higher pressure than the second vapour stream.

Typically, in the first flash stage the multi-component hydrocarbon stream is flashed to a temperature of at least 120° C., preferably at least 150° C., more preferably at least 170° C., e.g. between about 175° C. and about 190° C.

The elevated pressure may be between about 30 bar(a) and about 50 bar(a), preferably between about 40 bar(a) and about 50 bar(a), more preferably between about 46 bar(a) and about 50 bar(a).

The process in accordance with the first aspect of the invention may include separating at least a portion of the ethylene from the first ethylene-containing vapour stream. Thus, the first ethylene-containing vapour stream may be subjected to at least one ethylene recovery stage producing an ethylene-rich stream and an ethylene-poor multi-component hydrocarbon stream.

Typically, the ethylene recovery stage employs at least one distillation column. The ethylene recovery stage, and in particular said distillation column, may be operated at the same pressure as the first flash stage, minus any pressure drop caused by intervening process equipment. The ethylene recovery stage, and in particular said distillation column, may thus operate at a pressure in the range of about 10-18 bar(a), preferably about 10-15 bar(a).

The first ethylene-containing vapour stream is typically not recompressed before being fed into the ethylene recovery stage, but is preferably at least partially condensed before being fed into the ethylene recovery stage.

The process according to the second aspect of the invention may include the further step of recycling the ethylene-rich stream to the oligomerisation stage.

The ethylene-poor multi-component hydrocarbon stream may include a solvent for an ethylene oligomerisation catalyst.

The process may include combining the ethylene poor multi-component hydrocarbon stream from the ethylene recovery stage and the second vapour stream from the second flash stage. Typically, the pressure of the ethylene poor multi-component hydrocarbon stream is thus let down to the pressure of the second vapour stream.

The process may include recovering solvent from the combined streams of the ethylene poor multi-component hydrocarbon stream from the ethylene recovery stage and the second vapour stream from the second flash stage, e.g. by way of distillation.

The process in accordance with the first aspect of the invention may include heating the multi-component hydrocarbon stream to a desired temperature before flashing the multi-component hydrocarbon stream in the first flash stage.

Heating of the multi-component hydrocarbon stream may be effected in a heat exchanger, for example using high pressure steam or hot oil. Alternatively, or in addition, heating of the multi-component hydrocarbon stream may be effected by direct contact heating or mixing with a hot process stream, producing a combined stream which is then flashed in the first flash stage.

In at least one embodiment of the invention, at least some of the heat for the heating of the multi-component hydrocarbon stream is provided by the first ethylene-containing vapour stream.

The ethylene-poor multi-component hydrocarbon stream from the ethylene recovery stage may include 1-hexene, 1-octene and 1-butene. The multi-component hydrocarbon stream may also include cyclic by-products, aliphatic or aromatic solvent, ethane, very small if any quantities of methane, and polymer(s). Most methane and ethane in fact reports to the first ethylene-containing vapour stream.

In the oligomerisation stage, the ethylene is preferably oligomerised at an elevated pressure of at least 30 bar(a) and at an elevated temperature, typically at least 40° C. The elevated pressure may be between about 30 bar(a) and about 50 bar(a), preferably between about 40 bar(a) and about 50 bar(a), more preferably between about 46 bar(a) and about 50 bar(a). The elevated temperature of the oligomerisation stage is typically between about 40° C. and about 80° C., e.g. about 60° C.

In one embodiment of the invention, the process in accordance with the second aspect of the invention is a broad range ethylene oligomerisation process, employing a catalyst system and yielding a Schulz Flory or Poisson distribution of olefins. The olefins from this process find application as feedstock for detergents, plasticiser alcohols, linear alkyl benzenes and as comonomers for the production of polyethylene. Non-limiting examples of such catalyst systems are nickel based systems bearing α-diimine ligands and activated by a dialkyl aluminium halide cocatalyst (e.g. as described in WO 0010945), or nickel based systems having chelating ligands such as 2-diphenyl phosphine benzoic acid in combination with a borohydride reducing agent (e.g. as described in U.S. Pat. No. 3,676,523). Also possible is the use of trialkylaluminium catalysts for the production of a broad range of alpha olefins.

In a further embodiment of the invention, the process in accordance with the second aspect of the invention is predominantly a trimerisation of ethylene process. The trimerisation of ethylene to 1-hexene is a significant commercial operation. In addition to its use as a specific chemical, 1-hexene is extensively used in polymerisation processes either as a monomer or co-monomer. Non-limiting examples of ethylene trimerisation catalyst systems are provided in a review by Dixon, J. T., Green, M. J., Hess, F. M., and Morgan, D. H., Journal of Organometallic Chemistry, 2004, 689, 3641-3668. A few examples include the Phillips Cr/pyrollide/TEA system, the Dutch Polymer Institute Ti/benzyl substituted Cp/MAO system, the BP Cr/o-methoxyphenylPNP/MAO system and the Sasol Cr/SNS/MAO and Cr/o-alkylphenylPNP/MAO systems. Examples of ligand-free, tantalum-based catalyst systems have also been reported by Arteaga-Muller, R, Tsurugi, H., Saito, T, Yanagawa, M, Oda, S, and Mashima, K., J.A.C.S Communications, 2009, 131, 5370-5371.

In another embodiment of the invention, the process in accordance with the second aspect of the invention is predominantly a tetramerisation of ethylene process. As in the case of 1-hexene described above, 1-octene is also used as a comonomer in the production of linear low density polyethylene. Non limiting examples of selective ethylene tetramerisation catalyst systems include the ubiquitous Cr/PNP/MAO systems, beginning with PNP ligands containing no substituents on the phenyl rings attached to the P-atoms (e.g. as described in WO 2004/056479) and those with p-methoxy groups on the phenyl rings (e.g. as described in WO 2004/056480). In addition to this, PNP systems containing o-fluoro groups on the phenyl rings are described in US2008/0242811, and PNP systems bearing pendant donor atoms on the nitrogen linker are described in WO2007/088329. Multi-site PNP ligands are discussed in US2008/0027188.

In addition to the Cr/PNP systems, chromium systems bearing N,N-bidentate ligands (e.g. as described in US 2006/0247399) as well as systems containing PPN ligands (e.g. as described in WO2008/077911 and WO2008/077908) can be used. PNPNH as well as PNPNP ligands are described in WO2009/006979. Finally, chromium/PCCP/MAO systems are described in WO2008/088178 and WO2009/022770.

In a further embodiment, the process in accordance with the second aspect of the invention is predominantly both a trimerisation process and a tetramerisation process. In yet a further embodiment, the process in accordance with the second aspect of the invention is a tetramerisation of ethylene process in combination with a trimerisation of ethylene process, or broad range oligomerisation of ethylene process, as described in WO 2005/123884. The process may be a combination of a tetramerisation of ethylene and trimerisation of ethylene process as described in WO 2005/123884, WO 2007/057455 and WO 2006/108803. The process may also be a tandem oligomerisation/polymerisation process as discussed in WO 2004/056480.

In one embodiment of the process according to the second aspect of the invention, the catalyst is a dissolved transition metal compound catalyst, e.g. a chromium catalyst, with a heteroatomic or homoatomic, ligand, typically used with an activator. A number of dissolved transition metal compound catalysts have been developed for use to trimerise or tetramerise olefins, e.g. as disclosed in U.S. Pat. No. 4,668,838; EP 0668105; U.S. Pat. No. 5,750,817; U.S. Pat. No. 6,031,145; U.S. Pat. No. 5,811,618; WO 03/053890; WO 2004/056478; WO 2004/056477; WO 2004/056479; WO 2004/056480; WO 2005/123633 and WO 2007/007272, all of which are incorporated herein by reference.

Some of these catalysts are selective for $C_8$ and $C_8$ oligomeric products, e.g. 1-hexene and 1-octene, and the Applicant believes that such catalysts will be particularly advantageous for use with the process according to the second aspect of the invention as the selective production of 1-hexene and 1-octene from ethylene is commercially important.

In a preferred embodiment of the process in accordance with the second aspect of the invention the catalyst also includes one or more activators. Such an activator may be a compound that generates an active catalyst when the activator is combined with a source of transition metal and a ligating compound.

Suitable activators include aluminium compounds, organoboron compounds, organic salts, such as methyl lithium and methyl magnesium bromide, inorganic acids and salts, such as tetrafluoroboric acid etherate, silver tetrafluoroborate, sodium hexafluoroantimonate and the like.

Suitable aluminium compounds include compounds of the formula $Al(R^1)_3$ ($R^1$ being the same or different), where each $R^1$ is independently a $C_1$-$C_{12}$ alkyl, an oxygen containing moiety or a halide, aluminoxanes, and compounds such as $LiAlH_4$ and the like. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Examples of suitable aluminium compounds in the form of organoaluminium activators include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, $[Ph_3C][Al\{OC(CF_3)_3\}]$, methylaluminoxane (MAO), ethylaluminoxane (EAO), isobutylaluminoxane (iBuAO), modified alkylaluminoxanes such as modified methylaluminoxane (MMAO) and mixtures of the above-mentioned compounds.

Examples of suitable organoboron compounds are boroxines, $NaBH_4$, triethylborane, tris(pentafluorophenyl)borane, trityl tetrakis(pentafluorophenyl)borate, dimethylanilinium tetrakis(pentafluorophenyl)borate, tributyl borate, dialkylmethylammonium tetrakis(pentafluorophenyl)borate, where alkyl=$C_2$ to $C_{22}$, trialkylammonium tetrakis(pentafluorophenyl)borate, where alkyl=C2 to C22 and the like. These boron containing compounds may be used in conjunction with the $Al(R^1)_3$ compounds discussed above.

The activator may also be or contain a compound that acts as a reducing or oxidising agent, such as sodium or zinc metal and the like, or hydrogen or oxygen and the like.

In this specification the term "aluminoxanes" is used to denote a compound represented by the general formulae $(R^a—Al—O)_n$ and $R^b(R^c—Al—O)_n—AlR^d_2$ wherein $R^a$, $R^b$, $R^c$, and $R^d$ are independently a $C_1$-$C_{30}$ alkyl or halo-alkyl radical, for example methyl, ethyl, propyl, butyl, 2-methyl-propyl, pentyl, isopentyl, neopentyl, cyclopentyl, hexyl, iso-hexyl, cyclohexyl, heptyl, octyl, iso-octyl, 2-ethyl-hexyl, decyl, 2-phenyl-propyl, 2-(4-fluorophenyl)-propyl, 2,3-dimethyl-butyl, 2,4,4-timethyl-pentyl and dodecyl; and n has the value of 2 to 50. Preferably n is at least 4.

The activator may be selected from alkylaluminoxanes such as methylaluminoxane (MAO), high stability methylaluminoxane (MAO HS), ethylaluminoxane (EAO), isobutylaluminoxane (iBuAO) as well as modified alkylaluminoxanes such as modified methylaluminoxane (MMAO).

The transition metal source and the aluminoxane may be combined in proportions to provide Al/transition metal molar ratios from about 1:1 to 10 000:1, preferably from about 1:1 to 1000:1, and more preferably from 1:1 to 500:1.

The process in accordance with the second aspect of the invention may include the step of adding to the catalyst system a trialkylaluminium compound in amounts of between 0.01 to 1000 mol per mol of alkylaluminoxane.

In one embodiment of the process in accordance with the second aspect of the invention the oligomerisation catalyst includes a combination of
i) a source of Cr; and
ii) a ligating compound of the formula wherein:
$X^1$ and $X^2$ are independently selected from the group consisting of N, P, As, Sb, Bi, O, S and Se;
Y is a linking group between $X^1$ and $X^2$;
m and n are independently 0, 1 or a larger integer; and
$R^1$ and $R^2$ are independently hydrogen, a hydrocarbyl group or a heterohydrocarbyl group, and $R^1$ being the same or different when m>1, and $R^2$ being the same or different when n>1.

In this specification a heterohydrocarbyl group is a hydrocarbyl group which includes at least one heteroatom (that is not being H or C), and which organic compound binds with one or more other moieties through one or more carbon atoms of the organic compound and/or one or more heteroatoms of the organic compound. Organoheteryl groups and organyl groups (which include at least one heteroatom) are examples of heterohydrocarbyl groups.

Preferably the ligating compound is of the formula with $R^3$ to $R^7$ as defined above.

Preferably each of $R^3$ to $R^6$ is an alkyl (preferably methyl, ethyl or isopropyl) or aromatic (preferably phenyl or substituted phenyl).

Non limiting examples of the ligating compound are:
$(phenyl)_2PN(methyl)P(phenyl)_2$; $(phenyl)_2PN(ethyl)P(phenyl)_2$;
$(phenyl)_2PN(propyl)P(phenyl)_2$; $(phenyl)_2PN(butyl)P(phenyl)_2$;
$(phenyl)_2PN(pentyl)P(phenyl)_2$; $(phenyl)_2PN(hexyl)P(phenyl)_2$;
$(phenyl)_2PN(heptyl)P(phenyl)_2$; $(phenyl)_2PN(octyl)P(phenyl)_2$;
$(phenyl)_2PN(nonyl)P(phenyl)_2$; $(phenyl)_2PN(decyl)P(phenyl)_2$;
$(phenyl)_2PN(cyclopropyl)P(phenyl)_2$; $(phenyl)_2PN(cyclobutyl)P(phenyl)_2$;
$(phenyl)_2PN(cyclopentyl)P(phenyl)_2$; $(phenyl)_2PN(cyclohexyl)P(phenyl)_2$;
$(phenyl)_2PN(cycloheptyl)P(phenyl)_2$; $(phenyl)_2PN(cyclooctyl)P(phenyl)_2$;
$(phenyl)_2PN(cyclodecyl)P(phenyl)_2$; $(phenyl)_2PN(cyclododecyl)P(phenyl)_2$;
$(phenyl)_2PN(isopropyl)P(phenyl)_2$; $(phenyl)_2PN(isobutyl)P(phenyl)_2$;
$(phenyl)_2PN(secbutyl)P(phenyl)_2$; $(phenyl)_2PN(tertiarybutyl)P(phenyl)_2$;
$(phenyl)_2PN(neopentyl)P(phenyl)_2$; $(phenyl)_2PN(1,2-dimethyl-propyl)P(phenyl)_2$;
$(phenyl)_2PN(allyl)P(phenyl)_2$; $(phenyl)_2PN(methylheptyl)P(phenyl)_2$; $(phenyl)_2PN(1,5-dimethyl-heptyl)P(phenyl)_2$;
$(phenyl)_2PN(2-ethylhexyl)P(phenyl)_2$;
$(phenyl)_2PN(adamantyl)P(phenyl)_2$; $(phenyl)_2PN(adamantylmethyl)P(phenyl)_2$;

(phenyl)$_2$PN(3-trimethoxysilane-propyl)P(phenyl)$_2$; (phenyl)$_2$PN(indanyl)P(phenyl)$_2$;
(phenyl)$_2$PN(cyclohexylethyl)P(phenyl)$_2$; (phenyl)$_2$PN(2-methylcyclohexyl)P(phenyl)$_2$;
(phenyl)$_2$PN(cyclohexanemethyl)P(phenyl)$_2$; (phenyl)$_2$PN(benzyl)P(phenyl)$_2$;
(phenyl)$_2$PN(phenyl)P(phenyl)$_2$; (phenyl)$_2$PN((4-methoxy)-phenyl)P(phenyl)$_2$;
(phenyl)$_2$PN((3-methoxy)-phenyl)P(phenyl)$_2$;
(phenyl)$_2$PN((2-methoxy)phenyl)P(phenyl)$_2$;
(phenyl)$_2$PN((4-t-butyl)-phenyl)P(phenyl)$_2$;
(phenyl)$_2$PN((4-nitro)-phenyl)P(phenyl)$_2$; (phenyl)$_2$PN(1-naphthyl)P(phenyl)$_2$;
(phenyl)$_2$PN(2-naphthyl)P(phenyl)$_2$; (phenyl)$_2$PN(4-pyridyl)P(phenyl)$_2$
(phenyl)$_2$PN(3-(N-morpholine)-propyl)P(phenyl)$_2$;
(phenyl)$_2$PN(2-naphtyl-ethyl)P(phenyl)$_2$; (phenyl)$_2$PN(1-naphtylmethyl)P(phenyl)$_2$;
(phenyl)$_2$PN(diphenylmethyl)P(phenyl)$_2$;
(phenyl)$_2$PN(1,2-diphenyl-ethyl)P(phenyl)$_2$; (phenyl)$_2$PN(phenylethyl)P(phenyl)$_2$;
(phenyl)$_2$PN((2-methyl)phenyl)P(phenyl)$_2$;
(phenyl)$_2$PN((3-methyl)phenyl)P(phenyl)$_2$;
(phenyl)$_2$PN((4-methyl)phenyl)P(phenyl)$_2$;
(phenyl)$_2$PN((2,6-dimethyl)phenyl)P(phenyl)$_2$;
(phenyl)$_2$PN((2-ethyl)-phenyl)P(phenyl)$_2$;
(phenyl)$_2$PN(1,2,3,4-Tetrahydronaphthyl)P(phenyl)$_2$;
(phenyl)$_2$PN((2-methyl)cyclohexyl)P(phenyl)$_2$;
(phenyl)$_2$PN((3-methyl)cyclohexyl)P(phenyl)$_2$;
(phenyl)$_2$PN((4-methyl)cyclohexyl)P(phenyl)$_2$;
(phenyl)$_2$PN((2-ethyl)cyclohexyl)P(phenyl)$_2$;
(phenyl)$_2$PN((2-isopropyl)cyclohexyl)P(phenyl)$_2$;
(phenyl)$_2$PN((2,6-dimethyl)cyclohexyl)P(phenyl)$_2$;
(phenyl)$_2$PN(exo-2-norbornanyl)P(phenyl)$_2$; (phenyl)$_2$PN(isopinocampheyl)P(phenyl)$_2$;
(phenyl)$_2$PN(dimethylamino)P(phenyl)$_2$; (phenyl)$_2$PN(phthalimido)P(phenyl)$_2$;
(phenyl)$_2$PN(pyrrolyl)P(phenyl)$_2$; (phenyl)$_2$PN(trimethylsiyl)P(phenyl)$_2$;
(phenyl)$_2$PN(dimethyltertiarybutylsilyl)P(phenyl)$_2$;
[(phenyl)$_2$P]$_2$N(1,1'-bis(cyclohexyl)-4,4'-methylene))N[P(phenyl)$_2$]$_2$;
([(phenyl)$_2$P]$_2$N(1,6-hexylene-)N[P(phenyl)$_2$]$_2$;
(2,2',2''-triethylamino)[N[P(phenyl)$_2$]$_2$]$_3$; (4-biphenyl)PN(methyl)P(4-biphenyl)$_2$;
(2-naphthyl)$_2$PN(methyl)P(2-naphthyl)$_2$;
(4-methylphenyl)$_2$PN(methyl)P(4-methylphenyl)$_2$;
(3-methylphenyl)$_2$PN(methyl)P(3-methylphenyl)$_2$;
(2-naphthyl)$_2$PN(methyl)P(phenyl)$_2$;
(2-naphthyl)(phenyl)PN(methyl)P(2-naphthyl)(phenyl);
(2-naphthyl)$_2$PN(methyl)P(2-naphthyl)(phenyl);
(2-naphthyl)(phenyl)PN(methyl)P(phenyl)$_2$;
(2-methylphenyl)$_2$PN(methyl)P(2-methylphenyl)$_2$;
(2-ethylphenyl)$_2$PN(methyl)P(2-ethylphenyl)$_2$;
(2-isopropylphenyl)$_2$PN(methyl)P(2-isopropylphenyl)$_2$;
(2-methylphenyl)$_2$PN(ethyl)P(2-methylphenyl)$_2$;
(2-methylphenyl)$_2$PN(methyl)P(2-methylphenyl)(phenyl);
(2-methylphenyl)(phenyl)PN(isopropyl)P(2-methylphenyl)(phenyl);
(2-methylphenyl)$_2$PN(methyl)P(phenyl)$_2$;
(2-methylphenyl)(phenyl)PN(isopropyl)P(phenyl)$_2$;
(ethyl)$_2$PN(methyl)P(ethyl)$_2$; (ethyl)$_2$PN(isopropyl)P(ethyl)$_2$;
(ethyl)$_2$PN(tertiarybutyl)P(ethyl)$_2$; (methyl)$_2$PN(isopropyl)P(methyl)$_2$;
(isopropyl)$_2$PN(methyl)P(isopropyl)$_2$; (ethyl)$_2$PN(isopropyl)P(ethyl)(phenyl);
(ethyl)(phenyl)PN(isopropyl)P(ethyl)(phenyl); (ethyl)$_2$PN(isopropyl)P(phenyl)$_2$;
(ethyl)(phenyl)PN(isopropyl)P(phenyl)$_2$;
(2-thiopheneyl)$_2$PN(isopropyl)P(2-thiopheneyl)$_2$;
(diphenylphosphonite)N(isopropyl)(diphenylphosphonite);
(dibenzothiaphosphonine)N(isopropyl)(dibenzothiaphosphonine);
(dibenzooxaphosphonine)N(isopropyl)(dibenzooxaphosphonine);
(phenyl)$_2$PN(methyl)N(methyl)P(phenyl)$_2$; (phenyl)$_2$PN(ethyl)N(ethyl)P(phenyl)$_2$;
(phenyl)$_2$PN(phenyl)N(phenyl)P(phenyl)$_2$; (phenyl)$_2$PN(isopropyl)N(isopropyl)P(phenyl)$_2$;
(phenyl)$_2$PN(isopropyl)N(methyl)P(phenyl)$_2$; (phenyl)$_2$PN(isopropyl)N(methyl)P(phenyl)$_2$;
(4-methylphenyl)$_2$P—N(CH$_3$)N(CH$_3$)—P(4-methylphenyl)$_2$;
(3-methylphenyl)$_2$P—N(CH$_3$)N(CH$_3$)—P(3-methylphenyl)$_2$;
(2-methylphenyl)$_2$P—N(CH$_3$)N(CH$_3$)—P(2-methylphenyl)$_2$;
(2-ethylphenyl)$_2$P—N(CH$_3$)N(CH$_3$)—P(2-ethylphenyl)$_2$;
(2-isopropylphenyl)$_2$P—N(CH$_3$)N(CH$_3$)—P(2-isopropylphenyl)$_2$;
(2-methylphenyl)$_2$P—N(CH$_3$)N(CH$_3$)—P(2-methylphenyl)(phenyl);
(2-methlylphenyl)$_2$P—N(CH$_3$)N(CH$_3$)—P(phenyl)$_2$;
(ethyl)$_2$P—N(CH$_3$)N(CH$_3$)—P(ethyl)$_2$;
(methyl)$_2$P—N(CH$_3$)N(CH$_3$)—P(methyl)$_2$; (isopropyl)$_2$P—N(CH$_3$)N(CH$_3$)—P(isopropyl)$_2$;
(ethyl)$_2$P—N(CH$_3$)N(CH$_3$)—P(ethyl)(phenyl);
(ethyl)(phenyl)P—N(CH$_3$)N(CH$_3$)—P(ethyl)(phenyl);
(ethyl)$_2$P—N(CH$_3$)N(CH$_3$)—P(phenyl)$_2$; (ethyl)(phenyl)P—N(CH$_3$)N(CH$_3$)—P(phenyl)$_2$;
(2-thiopheneyl)$_2$P—N(CH$_3$)N(CH$_3$)—P(2-thiopheneyl)$_2$;
(2-naphthyl)$_2$P—N(CH$_3$)N(CH$_3$)—P(2-naphthyl)$_2$;
(4-biphenyl)$_2$P—N(CH$_3$)N(CH$_3$)—P(4-biphenyl)$_2$;
(phenyl)$_2$P-1,8-naphthyl-P(phenyl)$_2$;
(phenyl)$_2$P-9,10-phenanthrene-P(phenyl)$_2$;
(phenyl)$_2$P-4,5-phenanthrene-P(phenyl)$_2$; (phenyl)$_2$P—C(CH$_3$)$_2$—P(phenyl)$_2$; (phenyl)$_2$P—C(CH$_2$)$_2$—P(phenyl)$_2$; (phenyl)$_2$P-1,2-benzene-P(phenyl)$_2$;
(4-methylphenyl)$_2$P-1,2-benzene-P(4-methylphenyl)$_2$;
(3-methylphenyl)$_2$P-1,2-benzene-P(3-methylphenyl)$_2$;
(2-methylphenyl)$_2$P-1,2-benzene-P(2-methylphenyl)$_2$;
(2-ethylphenyl)$_2$P-1,2-benzene-P(2-ethylphenyl)$_2$;
(2-isopropylphenyl)$_2$P-1,2-benzene-P(2-isopropylphenyl)$_2$;
(2-methylphenyl)$_2$P-1,2-benzene-P(2-methylphenyl)(phenyl);
(2-methlylphenyl)$_2$P-1,2-benzene-P(phenyl)$_2$; (ethyl)$_2$P-1,2-benzene-P(ethyl)$_2$;
(methyl)$_2$P-1,2-benzene-P(methyl)$_2$; (isopropyl)$_2$P-1,2-benzene-P(isopropyl)$_2$;
(ethyl)$_2$P-1,2-benzene-P(ethyl)(phenyl);
(ethyl)(phenyl)P-1,2-benzene-P(ethyl)(phenyl);
(ethyl)$_2$P-1,2-benzene-P(phenyl)$_2$; (ethyl)(phenyl)P-1,2-benzene-P(phenyl)$_2$;
(2-thiopheneyl)$_2$P-1,2-benzene-P(2-thiopheneyl)$_2$;
(2-naphthyl)$_2$P-1,2-benzene-P(2-naphthyl)$_2$;
(4-biphenyl)$_2$P-1,2-benzene-P(4-biphenyl)$_2$; (phenyl)$_2$P—CH$_2$CH$_2$—P(phenyl)$_2$;
(4-methylphenyl)$_2$P—CH$_2$CH$_2$—P(4-methylphenyl)$_2$;
(3-methylphenyl)$_2$P—CH$_2$CH$_2$—P(3-methylphenyl)$_2$;
(4-methylphenyl)$_2$P—CH$_2$CH$_2$—P(4-methylphenyl)(phenyl);
(4-methylphenyl)(phenyl)P—CH$_2$CH$_2$—P(4-methylphenyl)(phenyl);

(4-methylphenyl)$_2$P—CH$_2$CH$_2$—P(phenyl)$_2$;
(4-methylphenyl)(phenyl)P—CH$_2$CH$_2$—P(phenyl)$_2$;
(2-methylphenyl)$_2$P—CH$_2$CH$_2$—P(2-methylphenyl)$_2$;
(2-ethylphenyl)$_2$P—CH$_2$CH$_2$—P(2-ethylphenyl)$_2$;
(2-isopropylphenyl)$_2$P—CH$_2$CH$_2$—P(2-isopropylphenyl)$_2$;
(2-methylphenyl)$_2$P—CH$_2$CH$_2$—P(2-methylphenyl)(phenyl);
(2-methlylphenyl)$_2$P—CH$_2$CH$_2$—P(phenyl)$_2$; (ethyl)$_2$P—CH$_2$CH$_2$—P(ethyl)$_2$;
(methyl)$_2$P—CH$_2$CH$_2$—P(methyl)$_2$; (isopropyl)$_2$P—CH$_2$CH$_2$—P(isopropyl)$_2$;
(ethyl)$_2$P—CH$_2$CH$_2$—P(ethyl)(phenyl); (ethyl)(phenyl)P—CH$_2$CH$_2$—P(ethyl)(phenyl);
(ethyl)$_2$P—CH$_2$CH$_2$—P(phenyl)$_2$; (ethyl)(phenyl)P—CH$_2$CH$_2$—P(phenyl)$_2$;
(2-thiopheneyl)$_2$P—CH$_2$CH$_2$—P(2-thiopheneyl)$_2$;
(phenyl)$_2$PB(phenyl)P(phenyl)$_2$;
(phenyl)$_2$PP(phenyl)P(phenyl)$_2$; (phenyl)$_2$PSi(methyl)$_2$P(phenyl)$_2$;
(phenyl)$_2$AsN(isopropyl)As(phenyl)$_2$; (phenyl)SN(isopropyl)S(phenyl); (phenyl)$_2$PN(isopropyl)S(phenyl); (phenyl)$_2$PN(isopropyl)As(phenyl)$_2$;
(phenyl)$_2$PN(isopropyl)P(=O)(phenyl)$_2$; (phenyl)$_2$P(=O)N(isopropyl)P(=O)(phenyl)$_2$;
(phenyl)$_2$PN(isopropyl)P(=S)(phenyl)$_2$; (phenyl)$_2$P(=S)N(isopropyl)P(=S)(phenyl)$_2$;
(phenyl)$_2$P(=O)N(isopropyl)P(=S)(phenyl)$_2$;
(4-trifluoromethylphenyl)$_2$PN(isopropyl)P(4-trifluoromethylphenyl)$_2$;
(4-chlorophenyl)$_2$PN(isopropyl)P(4-chlorophenyl)$_2$;
(4-methoxyphenyl)$_2$PN(methyl)P(4-methoxyphenyl)$_2$;
(4-methoxyphenyl)$_2$PN(isopropyl)P(4-methoxyphenyl)$_2$;
(3-methoxyphenyl)$_2$PN(methyl)P(3-methoxyphenyl)$_2$;
(4-methoxyphenyl)$_2$PN(isopropyl)P(4-methoxyphenyl)(phenyl);
(4-methoxyphenyl)(phenyl)PN(isopropyl)P(4-methoxyphenyl)(phenyl);
(4-methoxyphenyl)$_2$PN(isopropyl)P(phenyl)$_2$;
(4-methoxyphenyl)(phenyl)PN(isopropyl)P(phenyl)$_2$;
(4-methoxyphenyl)$_2$P—N(CH$_3$)N(CH$_3$)—P(4-methoxyphenyl)$_2$;
(3-methoxyphenyl)$_2$P—N(CH$_3$)N(CH$_3$)—P(3-methoxyphenyl)$_2$;
(4-methoxyphenyl)$_2$P—N(CH$_3$)N(CH$_3$)—P(4-methoxyphenyl)(phenyl);
(4-methoxyphenyl)(phenyl)P—N(CH$_3$)N(CH$_3$)—P(4-methoxyphenyl)(phenyl);
(4-methoxyphenyl)$_2$P—N(CH$_3$)N(CH$_3$)—P(phenyl)$_2$;
(4-methoxyphenyl)(phenyl)P—N(CH$_3$)N(CH$_3$)—P(phenyl)$_2$;
(4-methoxyphenyl)$_2$P-1,2-benzene-P(4-methoxyphenyl)$_2$;
(3-methoxyphenyl)$_2$P-1,2-benzene-P(3-methoxyphenyl)$_2$;
(4-methoxyphenyl)$_2$P-1,2-benzene-P(4-methoxyphenyl)(phenyl);
(4-methoxyphenyl)(phenyl)P-1,2-benzene-P(4-methoxyphenyl)(phenyl);
(4-methoxyphenyl)$_2$P-1,2-benzene-P(phenyl)$_2$;
(4-methoxyphenyl)(phenyl)P-1,2-benzene-P(phenyl)$_2$;
(3-methoxyphenyl)$_2$P(CH$_2$CH$_2$)P(3-methoxyphenyl)$_2$;
(3-methoxyphenyl)$_2$P(CH$_2$CH$_2$)P(3-methoxyphenyl)(phenyl);
(3-methoxyphenyl)(phenyl)P(CH$_2$CH$_2$CH$_2$)P(3-methoxyphenyl)(phenyl);
(3-methoxyphenyl)(phenyl)P(CH$_2$CH$_2$)P(3-methoxyphenyl)(phenyl);
(3-methoxyphenyl)(phenyl)P(CH$_2$)P(3-methoxyphenyl)(phenyl);
(3-methloxyphenyl)$_2$P(CH$_2$CH$_2$)P(phenyl)$_2$;
(3-methoxyphenyl)(phenyl)P(CH$_2$CH$_2$)P(phenyl)$_2$;
(4-methoxyphenyl)$_2$P(CH$_2$CH$_2$)P(4-methoxyphenyl)$_2$;
(4-methoxyphenyl)$_2$P(CH$_2$CH$_2$)P(4-methoxyphenyl)(phenyl);
(4-methoxyphenyl)(phenyl)P(CH$_2$CH$_2$CH$_2$)P(4-methoxyphenyl)(phenyl);
(4-methoxyphenyl)(phenyl)P(CH$_2$CH$_2$)P(4-methoxyphenyl)(phenyl);
(4-methoxyphenyl)(phenyl)P(CH$_2$)P(4-methoxyphenyl)(phenyl);
(4-methloxyphenyl)$_2$P(CH$_2$CH$_2$)P(phenyl)$_2$;
(4-methoxyphenyl)(phenyl)P(CH$_2$CH$_2$)P(phenyl)$_2$;
(2-methoxyphenyl)$_2$PN(methyl)P(2-methoxyphenyl)$_2$;
(2-methoxyphenyl)$_2$PN(ethyl)P(2-methoxyphenyl)$_2$;
(2-methoxyphenyl)$_2$PN(phenyl)P(2-methoxyphenyl)$_2$;
(2-methoxyphenyl)$_2$PN(methyl)N(methyl)P(2-methoxyphenyl)$_2$;
(2-methoxyphenyl)$_2$P(CH$_2$)P(2-methoxyphenyl)$_2$;
(2-methoxyphenyl)$_2$P(CH$_2$CH$_2$)P(2-methoxyphenyl)$_2$;
tri(2-methoxyphenyl)phosphane; tri(2-methoxymethoxyphenyl)phosphane;
(2-methoxyphenyl)$_2$PN(isopropyl)P(2-methoxyphenyl)(phenyl);
(2-methoxyphenyl)(phenyl)PN(isopropyl)P(2-methoxyphenyl)(phenyl);
(2-methloxyphenyl)$_2$PN(isopropyl)P(phenyl)$_2$;
(2-methoxyphenyl)(phenyl)PN(isopropyl)P(phenyl)$_2$;
(2-methoxyphenyl)$_2$PN(methyl)P(2-methoxyphenyl)(phenyl);
(2-methoxyphenyl)(phenyl)PN(methyl)P(2-methoxyphenyl)(phenyl);
(2-methloxyphenyl)$_2$PN(methyl)P(phenyl)$_2$;
(2-methoxyphenyl)(phenyl)PN(methyl)P(phenyl)$_2$;
(2-ethoxyphenyl)$_2$PN(methyl)P(2-ethoxyphenyl)$_2$;
(2-isopropoxyphenyl)$_2$PN(methyl)P(2-isopropoxyphenyl)$_2$;
(2-hydroxyphenyl)$_2$PN(methyl)P(2-hydroxyphenyl)$_2$;
(2-nitrophenyl)$_2$PN(methyl)P(2-nitrophenyl)$_2$;
(2-(dimethylamino)phenyl)$_2$PN(methyl)P(2-(dimethylamino)phenyl)$_2$;
(2,3-dimethoxyphenyl)$_2$PN(methyl)P(2,3-dimethoxyphenyl)$_2$;
(2,4-dimethoxyphenyl)$_2$PN(methyl)P(2,4-dimethoxyphenyl)$_2$;
(2,6-dimethoxyphenyl)$_2$PN(methyl)P(2,6-dimethoxyphenyl)$_2$;
(2,4,6-trimethoxyphenyl)$_2$PN(methyl)P(2,4,6-tri-methoxyphenyl)$_2$;
(2-methoxyphenyl)(2-methylphenyl)PN(methyl)P(2-methylphenyl)$_2$;
(2-methoxymethoxyphenyl)$_2$PN(methyl)P(2-methoxymethoxyphenyl)$_2$;
(2-methoxyphenyl)$_2$PN(methyl)P(2-methoxyphenyl)(phenyl);
(2-methoxyphenyl)(phenyl)PN(methyl)P(2-methoxyphenyl)(phenyl);
(2-methloxyphenyl)$_2$PN(methyl)P(phenyl)$_2$;
(2-methoxyphenyl)(phenyl)PN(methyl)P(phenyl)$_2$;
(2-methoxyphenyl)$_2$P—N(CH$_3$)N(CH$_3$)—P(2-methoxyphenyl)$_2$;
(2-methoxyphenyl)$_2$P-1,2-benzene-P(2-methoxyphenyl)$_2$;
(2-methoxyphenyl)$_2$P(CH$_2$CH$_2$)P(2-methoxyphenyl)$_2$;
(2-methoxyphenyl)$_2$P(CH$_2$CH$_2$)P(2-methoxyphenyl)(phenyl);
(2-methoxyphenyl)(phenyl)P(CH$_2$CH$_2$CH$_2$)P(2-methoxyphenyl)(phenyl);

(2-methoxyphenyl)(phenyl)P(CH$_2$CH$_2$)P(2-methoxyphenyl)(phenyl);
(2-methoxyphenyl)(phenyl)P(CH$_2$)P(2-methoxyphenyl)(phenyl);
(2-methloxyphenyl)$_2$P(CH$_2$CH$_2$)P(phenyl)$_2$;
(2-methoxyphenyl)(phenyl)P(CH$_2$CH$_2$)P(phenyl)$_2$;
(2-ethoxyphenyl)$_2$P(CH$_2$CH$_2$)P(2-ethoxyphenyl)$_2$;
(2-ethoxyphenyl)$_2$P(CH$_2$CH$_2$)P(2-ethoxyphenyl)(phenyl);
(2-ethoxyphenyl)(phenyl)P(CH$_2$CH$_2$CH$_2$)P(2-ethoxyphenyl)(phenyl);
(2-ethoxyphenyl)(phenyl)P(CH$_2$CH$_2$)P(2-ethoxyphenyl)(phenyl);
(2-ethoxyphenyl)(phenyl)P(CH$_2$)P(2-ethoxyphenyl)(phenyl);
(2-ethoxyphenyl)$_2$P(CH$_2$CH$_2$)P(phenyl)$_2$;
(2-ethoxyphenyl)(phenyl)P(CH$_2$CH$_2$)P(phenyl)$_2$;
(2-isopropoxyphenyl)$_2$P(CH$_2$CH$_2$)P(2-isopropoxyphenyl)$_2$;
(2-isopropoxyphenyl)$_2$P(CH$_2$CH$_2$)P(2-isopropoxyphenyl)(phenyl);
(2-isopropoxyphenyl)(phenyl)P(CH$_2$CH$_2$CH$_2$)P(2-isopropoxyphenyl)(phenyl);
(2-isopropoxyphenyl)(phenyl)P(CH$_2$CH$_2$)P(2-isopropoxyphenyl)(phenyl);
(2-isopropoxyphenyl)(phenyl)P(CH$_2$)P(2-isopropoxyphenyl)(phenyl);
(2-isopropoxyphenyl)$_2$P(CH$_2$CH$_2$)P(phenyl)$_2$;
(2-isopropoxyphenyl)(phenyl)P(CH$_2$CH$_2$)P(phenyl)$_2$;
(phenyl)$_2$PCH$_2$CH$_2$NHCH$_2$CH$_2$P(phenyl)$_2$; (ethyl)$_2$PCH$_2$CH$_2$NHCH$_2$CH$_2$P(ethyl)$_2$;
(phenyl)$_2$PCH$_2$CH$_2$NHCH$_2$CH$_2$P(ethyl)$_2$; (phenyl)(ethyl)PCH$_2$CH$_2$NHCH$_2$CH$_2$P(phenyl)$_2$;
(phenyl)SCH$_2$CH$_2$NHCH$_2$CH$_2$S(phenyl); (ethyl)$_2$PCH$_2$CH$_2$NHCH$_2$CH$_2$P(ethyl)$_2$;
(decyl)$_2$PCH$_2$CH$_2$NHCH$_2$CH$_2$P(decyl)$_2$; (phenyl)$_2$PCH$_2$CH$_2$NHCH$_2$CH$_2$S(ethyl);
(phenyl)$_2$PCH$_2$CH$_2$P(phenyl)CH$_2$CH$_2$P(phenyl)$_2$ and
(phenyl)$_2$PCH$_2$CH$_2$CH$_2$NHCH$_2$CH$_2$P(phenyl)$_2$.
(2-fluorophenyl)$_2$PN(isopropyl)P(2-fluorophenyl)$_2$, Ph$_2$PN(Me)P(2-methoxyphenyl)$_2$, (phenyl)$_2$PN(isopropyl)P(phenyl)NH(isopropyl), (phenyl)$_2$PN(isopropyl)P(phenyl)N(phenyl)H, (phenyl)$_2$PN(isopropyl)P(phenyl)N(t-butyl)H, (phenyl)$_2$PN(isopropyl)P(phenyl)N(CH(CH$_3$)(phenyl))H, (phenyl)$_2$PN(CH$_2$)(2-methoxyphenyl)P(phenyl)$_2$, (phenyl)$_2$PN(CH$_2$)$_2$(2-methoxyphenyl)P(phenyl)$_2$, (phenyl)$_2$PN(CH$_2$)$_3$(2-methoxyphenyl)P(phenyl)$_2$, Suitable ligand systems may also include mixtures of the above-mentioned ligands.

The ligating compound may include a polymeric moiety to render the reaction product of the source of transition metal and said ligating compound to be soluble at higher temperatures and insoluble at lower temperatures e.g. 25° C. This approach may enable the recovery of the complex from the reaction mixture for reuse and has been used for other catalyst as described by D. E. Bergbreiter et al., *J. Am. Chem. Soc.*, 1987, 109, 177-179. In a similar vein these transition metal catalysts can also be immobilised by binding the ligating compound to silica, silica gel, polysiloxane or alumina backbone as, for example, demonstrated by C. Yuanyin et al., *Chinese J. React. Pol.*, 1992, 1 (2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P(phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl)P(p-methoxyphenyl)$_2$)-benzene.

The ligating compounds may be prepared using procedures known to one skilled in the art and procedures forming part of the state of the art.

BRIEF DESCRIPTION OF THE DRAWINGS

The invention will now be described, by way of non-limiting examples, with reference to the accompanying diagrammatic drawings in which.

DETAILED DESCRIPTION OF THE INVENTION

Figure 1:
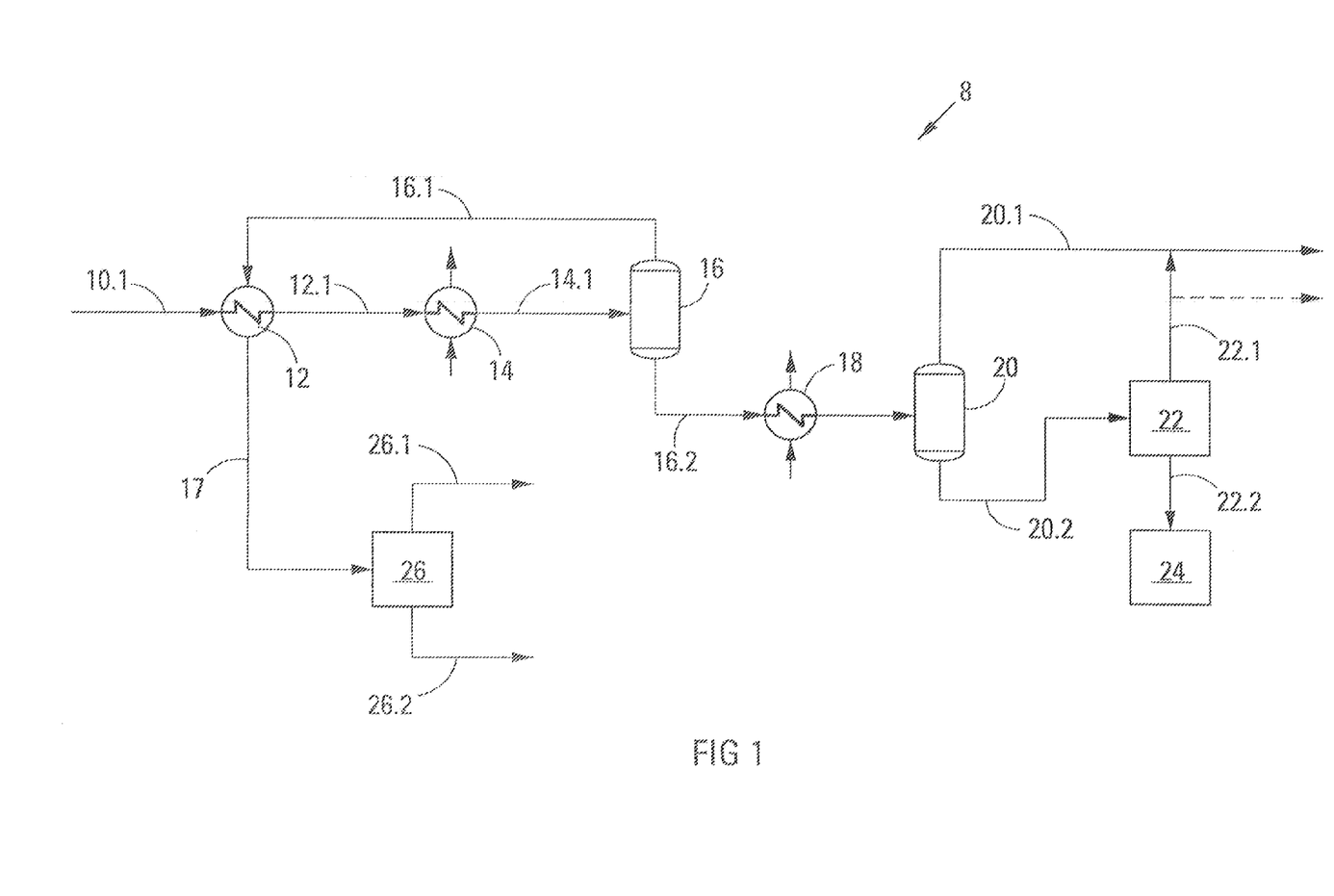
FIG. 1 shows one embodiment of a process in accordance with the invention to separate a multi-component hydrocarbon stream which includes ethylene and other components with at least some of the components being present in a plurality of phases.

Referring to FIG. 1 of the drawings, reference numeral 8 generally indicates a process in accordance with the invention to separate a multi-component hydrocarbon stream which includes ethylene and other components with at least some of the components being present in a plurality of phases. Such a process 8 can be incorporated into an ethylene oligomerisation process (not shown), which would include an oligomerisation stage in which a multi-component hydrocarbon stream is produced, the separation process 8 in which components of the multi-component stream are separated and in which ethylene is recovered, and further process stages, which may be entirely conventional and known to those skilled in the art.

The separation process 8 includes a first flash drum 16, a second flash drum 20 and a devolatiliser system 22. The separation process 8 further includes an ethylene recovery section 26.

A dissolved catalyst system including a transition metal source, optionally a ligating compound, a solvent and optionally a catalyst activator is used in the oligomerisation stage of the ethylene oligomerisation process together with ethylene. In particular, the catalyst system includes, a trimerisation or tetramerisation catalyst as described herein, an aliphatic solvent and an aluminoxane activator as described herein.

The oligomerisation stage of the ethylene oligomerisation process with the particular catalyst system primarily produces 1-hexene and 1-octene from ethylene. In other words, primarily trimerising and tetramerising of ethylene occur in the reactor. A multi-phase, multi-component hydrocarbon stream including 1-octene, ethane, methane, 1-butene, 1-hexene, hydrogen, solids and solvent as well as unreacted ethylene is removed from the ethylene oligomerisation stage and flows through a flow line 10.1 to the separation process 8. The multi-phase, multi-component hydrocarbon stream is typically at a temperature of about 60° C. and a pressure of about 48 bar(a).

In the separation process 8, the multi-phase, multi-component hydrocarbon stream in the flow line 10.1 is heated in a heat exchanger 12 and then fed by means of a flow line 12.1 to a high pressure steam heater 14 where the multi-phase, multi-component hydrocarbon stream is heated to a temperature of about 220° C. (using 42 bar steam or high pressure steam). The heated multi-phase, multi-component hydrocarbon stream is flashed through a valve (not shown) to a pressure typically between about 10 bar(a) and about 18 bar(a), more typically between about 10 bar(a) and about 16 bar(a) and fed through a flow line 14.1 to the first flash drum 16 where the multi-phase, multi-component hydrocarbon stream is separated.

The first flash drum 16 separates the multi-phase, multi-component hydrocarbon stream into a first ethylene-containing vapour stream (which thus includes most of the unreacted ethylene from the oligomerisation stage) withdrawn by means of a flow line 16.1 and a multi-phase stream which is predominantly liquid but which includes solids and gaseous components. The multi-phase stream is withdrawn from the first flash drum 16 by means of a flow line 16.2.

The pressure of the flash drum 16 is determined by economic considerations, taking into account ethylene lost to the multi-phase stream, recompression cost of recovered ethylene, capital expenditure and operating cost, and utility temperature constraints with respect to boil up of bottoms of the ethylene recovery section 26. The pressure of the flash drum 16 in the illustrated embodiment of FIG. 1 is however 14 bar(a).

Conventionally, a stream such as the multi-phase, multi-component hydrocarbon stream is flashed in a single process step. This ensures that the product is recovered at less severe conditions. However, the introduction of the two flash drums 16, 20, in series, in accordance with the invention, ensures that the first ethylene-containing vapour stream from the first flash drum 16 flowing through the flow line 16.1 is at a higher pressure, e.g. 14 bar(a). This has the advantageous effect that a small compression ratio is required in order to recycle the ethylene vapour back to the oligomerisation stage.

The introduction of the first flash step is thus to enable the ethylene to be recycled in a cost effective manner.

The multi-phase stream in the flow line 16.2 is heated again in a heat exchanger 18 to a temperature range of about 220 to 300° C. (typically using steam or hot oil) and flashed to a pressure of about 2 bar(a) in the second flash drum 20 which separates the multi-phase stream into a second vapour stream withdrawn by means of a flow line 20.1 and a bottoms stream containing predominantly solids and gases which is withdrawn by means of a flow line 20.2.

It is important to note that the heat exchanger 14 may utilise hot oil instead of steam. In such a case, the temperature of the multi-phase stream in the flow line 16.2 could be high enough (preferably at least 220° C. and even as high as 285° C.) for purposes of the second flash step such that the second heat exchanger 18 is not required.

The bottoms stream in the flow line 20.2 is fed to the devolatiliser system 22 which produces a solids stream which is withdrawn by means of a flow line 22.2 and a vapour stream which is withdrawn by means of a flow line 22.1. The vapour stream in the flow line 22.1 can be flared, or joined with the second vapour stream in the flow line 20.1 to be used further in the process 8 or recovered separately. The solids can be sent to a solids workup section 24, which may for example employ an underwater pelletiser to pelletise the solids.

The first ethylene-containing vapour stream in the flow line 16.1 from the first flash drum 16 is partially condensed in the heat exchanger 12 by heat exchange with the multi-phase, multi-component hydrocarbon stream in the flow line 10.1 and then enters the ethylene recovery section 26 as a partially condensed stream via flow line 17. The ethylene recovery section 26 typically employs a distillation column operating at a pressure of about 10-18 bar(a), preferably about 10-15 bar(a), to generate an ethylene rich vapour withdrawn by means of a flow line 26.1 and an ethylene poor multi-component hydrocarbon stream withdrawn by means of a flow line 26.2. The main purpose of the ethylene recovery section 26 is to give a predetermined required ethylene recovery for recycle back (by means of the flow line 26.1) to the oligomerisation stage.

The bottoms stream from the ethylene recovery section 26 (i.e. the ethylene poor multi-component hydrocarbon stream) includes oligomeric product, by-products and solvent and it is necessary to separate the solvent from the oligomeric product and by-products. Conventional separation techniques known to those skilled in the art may be employed to effect such separation.

The process 8, as illustrated, economically removes solids such as polyethylene, waxes, catalyst and catalyst deactivation products, from a multi-component multi-phase hydrocarbon stream which includes ethylene and desirable oligomeric products. This allows the multi-component multi-phase hydrocarbon stream to be subjected to distillation to recover unreacted ethylene (thereby improving the economics of the ethylene oligomerisation process) and to separate the oligomeric products into desirable fractions.

Figure 2:
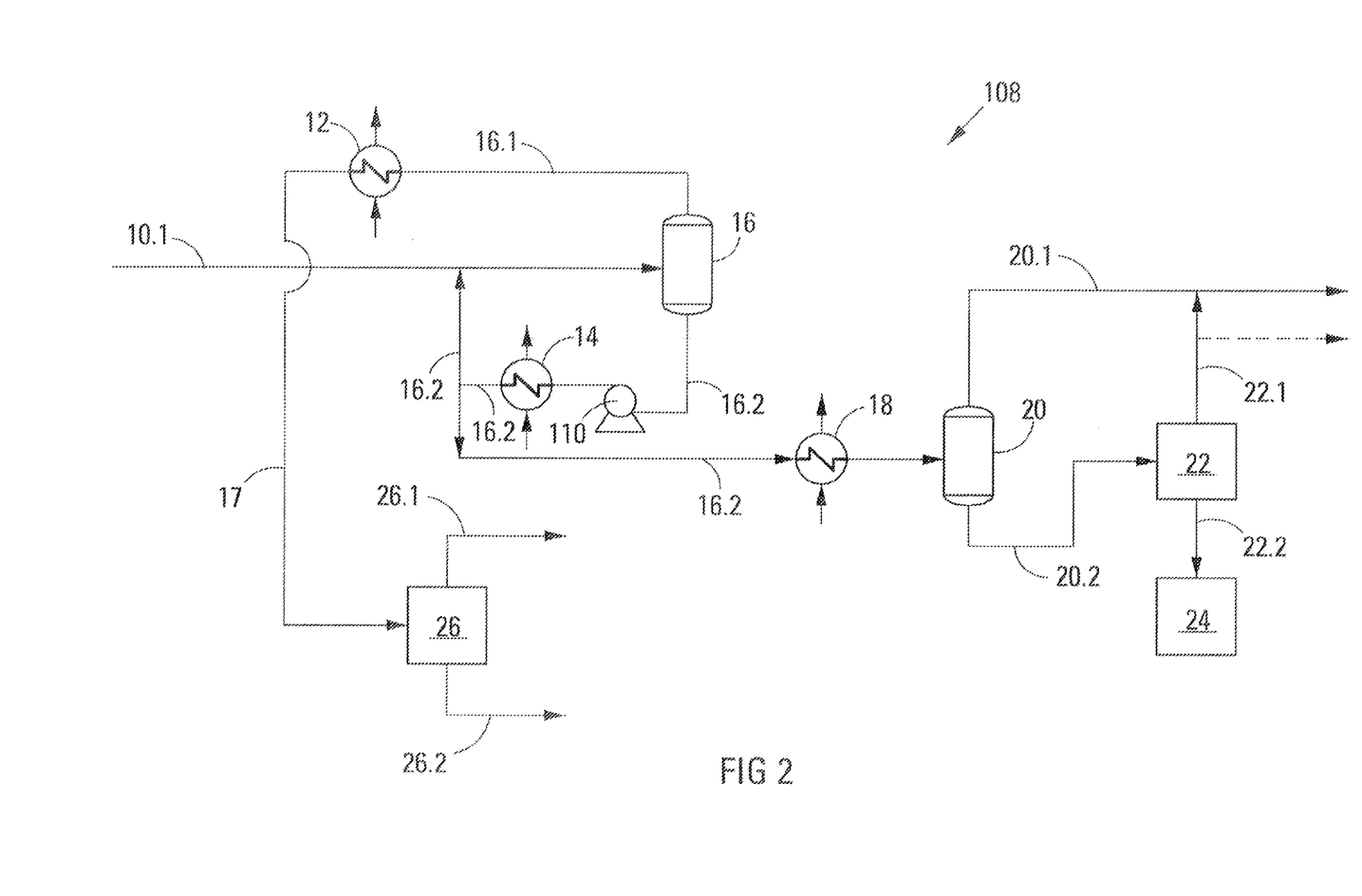
FIG. 2 shows another embodiment of a process in accordance with the invention to separate a multi-component hydrocarbon stream which includes ethylene and other components with at least some of the components being present in a plurality of phases.

Referring to FIG. 2 of the drawings, another embodiment of a process in accordance with the invention to separate a multi-component hydrocarbon stream which includes ethylene and other components with at least some of the components being present in a plurality of phases, is shown and indicated by reference numeral 108. In the process 108 of FIG. 2, the same reference numerals are used to indicate the same or similar process features as are used in FIG. 1 in relation to the process 8, unless otherwise indicated.

Unlike the process 8, the process 108 includes a further pump 110 in the flow line 16.2 and the flow line 16.2 downstream from the pump 110 branches off to join the flow line 10.1. Further differences are that the heat exchanger 12 in the process 108 is not located in the flow line 10.1, and the heat exchanger 14 is located in the flow line 16.2 downstream from the pump 110.

The process 108 is operated similarly to the process 8, with a few changes. In the process 108 the multi-phase stream withdrawn from the first flash drum 16 by means of the flow line 16.2 is first routed to the pump 110 where the multi-phase stream is pumped up to a pressure sufficient to overcome any pressure drop in the flow line 16.2 and in the heat exchanger 14 to bring the pressure in the flow line 16.2 up to the pressure in the flow line 10.1 (e.g. 48 bar(a)) so that where the flow lines 10.1 and 16.2 join, the pressures are substantially equal.

In the heat exchanger 14, the multi-phase stream in flow line 16.2 from the first flash drum 16 is heated to a temperature in excess of 190° C. (e.g. 199° C.) using high pressure steam and a portion of said heated stream in the flow line 16.2 is combined with the multi-phase, multi-component hydrocarbon stream in the flow line 10.1 coming from an ethylene oligomerisation stage (not shown). The mass flow rate through the flow line 16.2 joining the flow line 10.1 is about ten times the mass flow rate through flow line 10.1. The flow rate and the temperature of the heated stream in flow line 16.2 are sufficiently high so that when the heated stream in flow line 16.2 is mixed with the multi-component hydrocarbon stream in the flow line 10.1 coming from an ethylene oligomerisation stage it results in a combined stream temperature typically between 180 and 220° C., e.g. 190° C. The heated combined multi-phase, multi-component hydrocarbon stream at about 190° C. is flashed through a valve (not shown) to a pressure typically between about 10 bar(a) and about 16 bar(a), e.g. 15.5 bar(a) and a temperature of about 186° C. and then fed to the first flash drum 16 where the multi-phase, multi-component hydrocarbon stream is separated.

The remaining portion of the multi-phase stream exiting the heat exchanger 14 and not recycled to the flash drum 16 is passed through the flow line 16.2 to be further heated in the heat exchanger 18, as is the case for the process 8.

The recycle flow rate of the multi-phase stream to the flash drum 16 and the outlet temperature of the heat exchanger 14 may be manipulated to vary the temperature of the heated combined multi-phase, multi-component hydrocarbon stream in the flow line 10.1 to the first flash drum 16.

The first flash drum 16 separates the multi-phase, multi-component hydrocarbon stream into a first ethylene-rich vapour stream (which thus includes most of the unreacted ethylene from the oligomerisation stage) withdrawn by means of the flow line 16.1 and the multi-phase stream which is predominantly liquid but which includes solids and gaseous components. The multi-phase stream is withdrawn from the first flash drum 16 by means of the flow line 16.2, as described hereinbefore.

As for the process 8, the pressure of the flash drum 16 is determined by economic considerations, taking into account ethylene lost to the multi-phase stream, recompression cost of recovered ethylene, capital expenditure and operating cost, and utility temperature constraints with respect to boil up of the ethylene recovery section 26 bottoms. The pressure of the flash drum 16 in the embodiment illustrated in FIG. 2 is however 15.5 bar(a).

Conventionally, as mentioned hereinbefore, a stream such as the multi-phase, multi-component hydrocarbon stream is flashed in a single process step. This ensures that the product is recovered at less severe conditions. However, the introduction of the two flash drums 16, 20, in series, in accordance with the invention, ensures that the first ethylene-containing vapour stream from the first flash drum 16 flowing through the flow line 16.1 advantageously has a pressure of 15.5 bar(a), which means that only a small compression ratio is required in order to recycle the ethylene vapour back to the oligomerisation stage.

As is the case for the process 8, the introduction of the first flash step is thus to enable the ethylene to be recycled in a cost effective manner.

The multi-phase stream in the flow line 16.2 is further heated in the heat exchanger 18 to a temperature of about 285° C. (typically using hot oil) and flashed to a pressure of about 4 bar(a) in the second flash drum 20 which separates the multi-phase stream into a second vapour stream withdrawn by means of the flow line 20.1 and a bottoms stream containing predominantly solids and gases which is withdrawn by means of the flow line 20.2.

It is important to note that the heat exchanger 14 also may employ hot oil instead of steam as a heat transfer medium. In such a case, the temperature of the multi-phase stream in the flow lines 16.2 downstream of the heat exchanger 14 could be high enough for purposes of the second flash step such that the heat exchanger 18 is not required.

The bottoms stream in the flow line 20.2 of the process 108 is treated in the same fashion as the bottoms stream in the flow line 20.2 of the process 8.

The first ethylene-containing vapour stream in the flow line 16.1 from the first flash drum 16 is partially condensed in the heat exchanger 12 by heat exchange with low pressure steam condensate, producing low pressure steam, and then enters the ethylene recovery section 26 as a partially condensed stream via flow line 17. The ethylene recovery section 26 of the process 108 operates in the same fashion as the ethylene recovery section 26 of the process 8.

Similar to the process 8, the process 108, as illustrated, economically removes solids such as polyethylene, waxes, catalyst and catalyst deactivation products, from a multi-component multi-phase hydrocarbon stream which includes ethylene and desirable oligomeric products. This allows the multi-component multi-phase hydrocarbon stream to be subjected to distillation to recover unreacted ethylene (thereby improving the economics of the ethylene oligomerisation process) and to separate the oligomeric products into desirable fractions.

The process 8, 108 of the invention, as illustrated, ensures the recovery of ethylene at a relatively high intermediary pressure which is cost effective. The thermodynamically optimum route would be to take the multi-component multi-phase hydrocarbon stream from an ethylene oligomerisation stage and flash it in one single separation step by flashing the stream down to 1 to 2 bar(a). In this way, the reactor products can be recovered at less severe conditions. However, the ethylene would have to be compressed up to the pressure of the oligomerisation stage again at a high compression ratio which is expensive. To overcome this problem, an intermediary flash is introduced (i.e. flash drum 16) in which the multi-component multi-phase hydrocarbon stream is flashed at a medium pressure so that most of the ethylene is recovered at a higher pressure of at least 10 bar(a), e.g. about 14 bar(a)-16 bar(a) and a lower compression ratio is therefore required to ensure that recycled ethylene is fed into the oligomerisation stage at the required pressure. Further, the process 8, 108 recovers heat which is re-integrated into the process. This further optimises the operating costs of the process 8, 108.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

The invention claimed is:

1. A process to separate a multi-component hydrocarbon stream which includes ethylene and other components with at least some of the components being present in a plurality of phases, the process including
    in a first flash stage, flashing the multi-component hydrocarbon stream, from an elevated pressure of more than 18 bar(a) and a temperature of more than 180° C. to a pressure in the range of 10-18 bar(a), producing a first ethylene-containing vapour stream at a pressure in the range of 10-18 bar(a) and a multi-phase stream which includes some ethylene;
    in a second flash stage, flashing the multi-phase stream to a pressure of less than 6 bar(a), producing a second vapour stream at a pressure of less than 6 bar(a) and a bottoms stream;
    removing the first ethylene-containing vapour stream from the first flash stage and the second vapour stream from the second flash stage;
    separating at least a portion of the ethylene from the first ethylene-containing vapour stream by subjecting the first ethylene-containing vapour stream to at least one ethylene recovery stage producing an ethylene-rich stream and an ethylene-poor multi-component hydrocarbon stream; and
    removing the bottoms stream from the second flash stage.

2. The process as claimed in claim 1, in which the multi-phase stream is flashed in the second flash stage to a pressure of between 1 bar(a) and 6 bar(a).

3. The process as claimed in claim 1, in which, in the first flash stage, the multi-component hydrocarbon stream is flashed from an elevated temperature of at least 185° C. and an elevated pressure of more than 30 bar(a), the first ethylene-containing vapour stream defining a higher mass flow of ethylene and being at a higher pressure than the second vapour stream.

4. The process as claimed in claim 1, in which the ethylene recovery stage employs at least one distillation column operated at a pressure in the range of 10-18 bar(a), with the first ethylene-containing vapour stream not being recompressed before being fed into the ethylene recovery stage, but being at least partially condensed before being fed into the ethylene recovery stage.

5. The process as claimed in claim 1, in which the ethylene-poor multi-component hydrocarbon stream includes a solvent for an ethylene oligomerisation catalyst, the process further including combining the ethylene poor multi-component hydrocarbon stream from the ethylene recovery stage and the second vapour stream from the second flash stage and recovering solvent from the combined streams by way of distillation.

6. The process as claimed in claim 5, in which the pressure of the ethylene poor multi-component hydrocarbon stream is let down to the pressure of the second vapour stream.

7. The process as claimed in claim 1, which includes heating the multi-component hydrocarbon stream to a temperature of at least 180° C. before flashing the multi-component hydrocarbon stream in the first flash stage, with at least some of the heat for the heating of the multi-component hydrocarbon stream being provided by the first ethylene-containing vapour stream.

8. The process as claimed in claim 7, in which the heating of the multi-component hydrocarbon stream is by means of indirect heat exchange with a heating medium or hot process stream, or by direct contact heating or mixing with a hot process stream.

9. An ethylene oligomerisation process, the process including
    in an oligomerisation stage, oligomerising ethylene and withdrawing a multi-component hydrocarbon stream of different phases which include oligomeric product, polymeric product, and unreacted ethylene;
    heating the multi-component hydrocarbon stream to a temperature in excess of 180° C.;
    separating the multi-component hydrocarbon stream in accordance with a separation process as claimed in claim 1, producing said first ethylene-containing vapour stream; and
    feeding the first ethylene-containing vapour stream to said ethylene recovery stage producing said ethylene-rich stream and said ethylene-poor multi-component hydrocarbon stream which includes oligomeric and/or polymeric product.

10. The process as claimed in claim 9, in which the multi-component hydrocarbon stream is heated to a temperature of at least 180° C. before flashing the multi-component hydrocarbon stream in the first flash stage, with at least some of the heat for the heating of the multi-component hydrocarbon stream being provided by the first ethylene-containing vapour stream.

11. The process as claimed in claim 9, which includes recycling the ethylene-rich stream to the oligomerisation stage.

12. The process as claimed in claim 9, in which, in the oligomerisation stage, the ethylene is oligomerised at an elevated pressure of at least 30 bar(a) and at an elevated temperature of at least 40° C.

* * * * *